United States Patent
Soulier et al.

(10) Patent No.: US 6,461,648 B2
(45) Date of Patent: Oct. 8, 2002

(54) PROCESS FOR THE PURIFICATION OF A RED FRUIT EXTRACT CONTAINING ANTHOCYANOSIDES, EXTRACT OBTAINED FROM THE PROCESS AND USE OF SAID EXTRACT

(75) Inventors: Chrystèle Soulier, Veyre Monton; Dominique DuFour, Beaumont, both of (FR)

(73) Assignee: Ferlux (Societe Anonyme), Cournon D'Auvergne (FR)

( * ) Notice: Subject to any disclaimer, the term of this patent is extended or adjusted under 35 U.S.C. 154(b) by 0 days.

(21) Appl. No.: 09/929,269

(22) Filed: Aug. 14, 2001

(65) Prior Publication Data

US 2002/0018821 A1 Feb. 14, 2002

Related U.S. Application Data

(63) Continuation of application No. PCT/FR00/00275, filed on Feb. 7, 2000.

(51) Int. Cl.$^7$ ................................................ A61K 35/78
(52) U.S. Cl. .................................................... 424/777
(58) Field of Search .......................................... 424/777

(56) References Cited

U.S. PATENT DOCUMENTS 5,200,186 A    4/1993  Gabetta et al. ............. 424/195

FOREIGN PATENT DOCUMENTS

| EP | 0 412 300 | 2/1991 |
|----|-----------|--------|
| FR | 2 299 385 | 8/1976 |
| FR | 2 456 747 | 12/1980 |
| FR | 2 641 283 | 7/1990 |
| GB | 1 235 379 | 6/1971 |

*Primary Examiner*—Herbert J. Lilling
(74) *Attorney, Agent, or Firm*—Heslin Rothenberg Farley & Mesiti P.C.

(57) ABSTRACT

Process for purifying a red fruit extract containing anthocyanosides, according to which:
  said extract is taken up in an aqueous solution;
  the aqueous extract is cooled until it reaches a homogeneous temperature of less than 15° C.;
  after filtering the aqueous extract, the permeate obtained is recovered and loaded onto a macrocrosslinked polymeric resin;
  the resin is then rinsed with demineralized water;
  then the resin obtained is eluted with an alcoholic eluting solution;
  finally, the eluate obtained is concentrated and then dried.

7 Claims, 2 Drawing Sheets

PROCESS FOR THE PURIFICATION OF A RED FRUIT EXTRACT CONTAINING ANTHOCYANOSIDES, EXTRACT OBTAINED FROM THE PROCESS AND USE OF SAID EXTRACT

CROSS REFERENCE TO RELATED APPLICATIONS

This application is a continuation of PCT application PCT/FR00/00275 filed Feb. 7, 2000 designating the United States, and published in French as WO 00/47596 on Aug. 17, 2000. PCT/FR99/00275 claimed the priority of French application FR 9901959 filed Feb. 15, 1999. The entire disclosures of both are incorporated herein by reference.

The invention relates to a process for purifying a red fruit extract containing anthocyanosides. It also relates to the extract obtained by said process and its use.

In the remainder of the description and in the claims, "red fruit" denotes in particular elderberry (*Sambucus nigra*), blackcurrant (*Ribes nigrum*), redcurrant (*Ribes rubrum*), mulberry (*Morus nigra*), grape (*Vitis vinifera*), and more particularly bilberry (*Vaccinium myrtillus* and other species of the genus Vaccinium), this being without limitation.

In general, the term "anthocyanosides" denotes a heterosaccharide resulting from the combination of an anthocyanic genin with one or more glycosidic groups. These anthocyanosides exist in the form of monomers, but also of dimers, oligomers and polymers according to an increasing degree of polymerization. The anthocyanoside-anthocyanoside bond occurs between the C4 of the C nucleus and the C8 of the A nucleus.

In the present case, anthocyanosides denote the structures in the form of monomers whose molecular weight varies from 400 to 600 Daltons. Certain forms of dimers may also be present whose molecular weight may be up to about 1000 Daltons.

Red fruits are rich in pigments called anthocyanosides which have been demonstrated to have an effect on blood microcirculation by acting in particular as vitamin P factor, as antioxidant, as platelet aggregation inhibitor and as antifree radical agent. These properties have been recognized for the treatment of disorders involving retinal circulation, in the treatment of functional disorders of hair brittleness and visual disorders of vascular origin. These properties have also been demonstrated for the treatment of hesperanopia and myopia, in the proprietary medicinal products marketed under the trade marks DIFRAREL® 100 and DIFRAREL® E by LEURQUIN MEDIOLANUM laboratories.

Several processes for extracting anthocyanosides from plants or from plant portions have been proposed.

Document FR-A-2 299 385 thus describes a process for extracting anthocyanins from grape marc comprising an extraction step proper, followed by a step for concentrating the extract obtained.

According to this process, the extraction step consists in treating the marcs with an acidic aqueous extraction solution (pH=2) supplemented with $SO_2$ in the hot state (between 40 and 55° C.). The clear solution obtained, containing the anthocyanosides, but also the acids, salts, polyphenols and proteins, is then concentrated. To do this, it is loaded onto a resin. The resin is then eluted with an eluting solution containing either a ketone, an amide or an aqueous solution of an alkali or alkaline-earth metal hydroxide. The anthocyanins are finally separated from the eluate obtained.

It is evident from the examples described, in particular example 1, that starting with an extract containing 120 mg of anthocyanins per liter, an extract is obtained at the outlet of the resin which comprises 800 mg per liter of anthocyanins, that is to say an extract concentrated 6.6 fold.

However, even if the process used makes it possible to markedly increase the concentration of anthocyanosides in the extract, this concentration is not at all indicative of a purification of the anthocyanosides.

Furthermore and in particular, the initial extraction of the anthocyanosides with a solvent supplemented with $SO_2$ leads to the attachment of the anthocyanosides to the resin in a modified form, which is therefore capable of disrupting the physicochemical characteristics of the anthocyanoside and therefore its activity.

More recently, a process for extracting and then purifying anthocyanosides from bilberries was proposed in the document EP-A-412 300.

The extraction step proper consists in placing frozen fruits in contact with an aqueous solution of methanol, each extraction extending over a period of four hours.

The extract obtained is then purified. To do this, it is first concentrated under vacuum, the resulting concentrate then being supplemented with sodium bisulfite. A bond is then formed between the anthocyanosides and the bisulfite ions. After stirring for three hours and neutralization by adding a sodium hydroxide solution, the extract obtained is loaded onto a column of a nonionogenic polymer resin and then the column is eluted with purified water. The eluate is then acidified to pH=1 with concentrated hydrochloric acid (HCl). To remove the $SO_2$, nitrogen is then bubbled through the solution obtained so as to dissociate the anthocyanosides-bisulfite complex. This dissociation leads to the release of sulfur dioxide. The aqueous solution is then extracted with butanol. The butanolic solution is supplemented with 14 volumes of ethyl acetate. After allowing to stand overnight, the precipitate is dried at 40° C.

As above, the process used still requires the use of bisulfite ions leading to the formation of an anthocyanoside-bisulfite complex capable of altering the physicochemical properties of the desired anthocyanosides.

Furthermore, the use of nitrogen for regenerating the anthocyanosides results in emissions of sulfur dioxide which can create environmental problems and problems of cumbersome treatments of the discharges.

It is finally also important to emphasize the multitude of solvents used (methanol, butanol and ethyl acetate) and the cumbersome chemical treatments which this extraction process involves: use of $SO_2$, NaOH, acidification to pH=1 with concentrated HCl and use of nitrogen.

A process for extracting coloring substances and more particularly a process for extracting anthocyanosides from the berries of fruits, bilberries, blackcurrants or cranberries requiring in particular the use of a weakly polar supercritical solvent which is subsequently distilled off is known from patent FR 2641983. The extraction residue is purified by the customary physical means, in particular by chromatography on a polyamide column and then elution with hydrochloric methanol.

The anthocyanosides thus obtained and in particular those of bilberry are active ingredients of medicaments.

From this prior state of the art, the invention relates to a process for purifying an extract of red fruits containing anthocyanosides capable of solving the following problems:

dispensing with the use of any $SO_2$-type additive which is likely to modify the structure and the physicochemical characteristics of the anthocyanosides extracted;

avoiding any emission of harmful substances and in particular of sulfur dioxide;

increasing the concentration of anthocyanosides in the purified extract obtained;

carrying out a purification without structural modification of the anthocyanosides;

reducing as much as possible the quantity of residual solvents contained in the purified extract;

obtaining an extract in which the residual solvents are clearly identified, and the low quantity of which complies with the ICH (International Conference on Harmonization of Technical Requirements for Registration of Pharmaceuticals for Human Use) guidelines.

Figure 1:
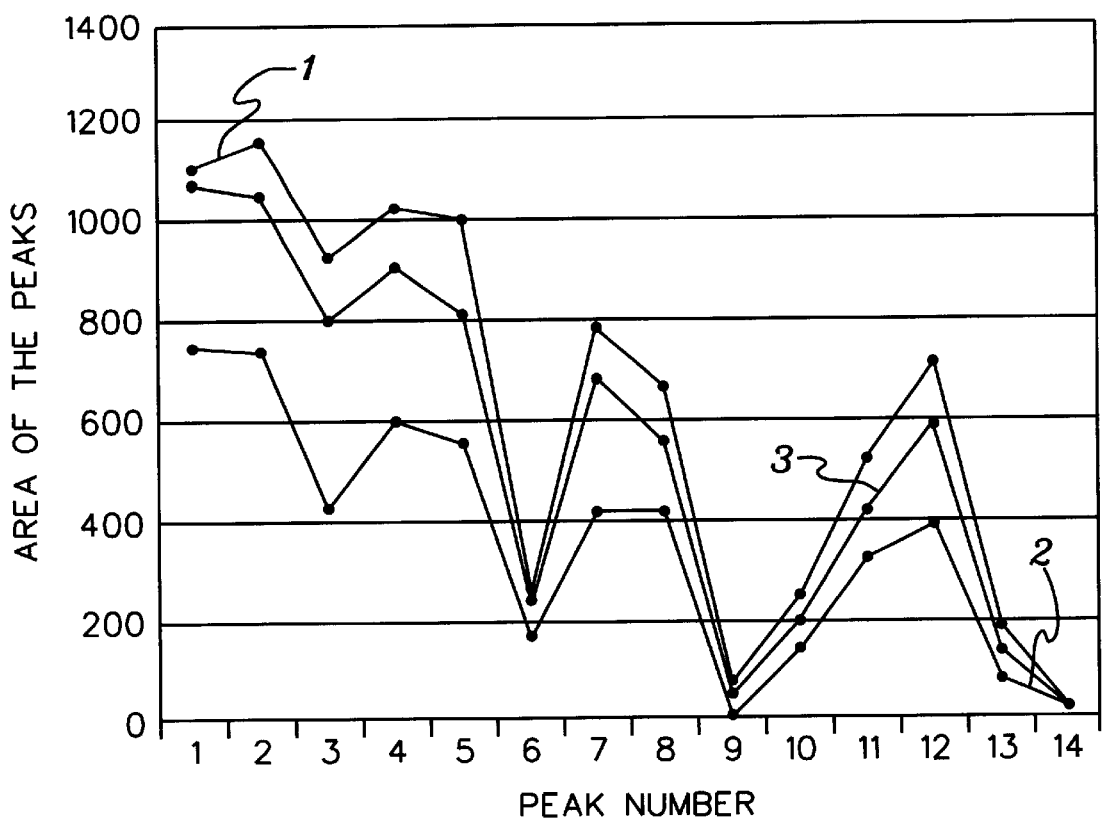
FIG. 1 is a graph of peak area vs. peak number which compares the HPLC chromatogram of the final extract of Example 1, in accordance with the process of the present invention, relative to that of the original fruit and that of the original pulp.

To do this, the subject of the invention is a process for purifying a red fruit extract containing anthocyanosides, according to which:

said extract is taken up in an aqueous solution;

the aqueous extract is cooled until it reaches a homogeneous temperature of less than 15° C.;

after filtering the aqueous extract, the permeate obtained is recovered and loaded onto a macrocrosslinked polymeric resin;

the resin is then rinsed with demineralized water;

then the resin obtained is eluted with an alcoholic eluting solution;

finally, the eluate obtained is concentrated and then dried.

In this way, by dispensing with any solvent supplemented with $SO_2$, the process of purification of the invention, carried out under gentle conditions, causes no modification of the native physicochemical characteristics, and therefore no denaturation of the anthocyanosides extracted. This characteristic may be confirmed by the superposition of the HPLC chromatographic profiles as a function of the retention time for the extract, on the one hand, and for the starting red fruit, on the other hand.

Furthermore, it is observed that the combination of various steps of the process, and in particular the cooling step followed by the filtration and passage over a resin, leads, quite surprisingly, to the extracted anthocyanoside titer in the final dry extract being considerably increased. For a temperature of the aqueous extract greater than 15° C., sufficient purification of the anthocyanosides is not obtained.

In a first embodiment of the invention, the process of purification is carried out on an alcoholic red fruit extract obtained according to the following process:

the pulp is first of all separated from the whole red fruits;

said pulp is then brought into contact with an alcoholic extraction solution;

then the solid phase is separated from the liquid phase;

finally, at least some, but preferably the major portion of the residual alcohol contained in the liquid phase is evaporated under vacuum so as to obtain an alcoholic concentrate.

Advantageously, the solvent used for the alcoholic extraction is chosen from the group comprising methanol, ethanol, butanol and acetone.

In practice, the alcoholic extraction is carried out at room temperature in at least two successive steps, each lasting 20 minutes. The solvent is then evaporated off. In addition, it is also possible to envisage carrying out the extraction of the anthocyanosides not from the pulp alone, but from whole fruits.

Furthermore, the solid phase/liquid phase separation may be carried out by any known means, in particular centrifugation.

According to a second embodiment of the invention, the process of purification is carried out starting with extracts of red fruits which are commercially available or with prepurified anthocyanoside extract, each provided in liquid or powdered form. In this case, the fruit extract or the prepurified extract may then be taken up, before the purification step, either with alcohol, in particular methanol, or with water.

In the process of purification of the invention, the cooling of the red fruit extract is advantageously carried out until the temperature of said extract is homogeneous and less than 10° C., preferably less than 5° C., this temperature being maintained for at least twelve hours.

As regards the step of filtration of the aqueous extract, it may be carried out on a cellulose filter or a stainless steel gauze with a cut-off of between 0 and 100 micrometers or equivalent.

As already stated, the permeate obtained from the filtration step is then loaded onto an adsorbent macrocrosslinked resin.

Moreover, in order to further increase the titer and the concentration of anthocyanosides in the final extract, the alcoholic solution with which the anthocyanosides are eluted from the resin is preferably an aqueous solution of ethanol whose ethanol concentration is between 10 and 90%, advantageously close to 40%.

The eluate obtained is concentrated at a controlled temperature in the region of 30° C. and then freeze-dried or spray-dried so as to obtain a powder.

It is moreover observed that the powder obtained contains a very small residual quantity of alcoholic solvent, of less than 3000 ppm for methanol (if the purification is carried out from a methanolic extract) and less than 2000 ppm for ethanol. These residual solvents are identified by GC and are the only ones contained in the final powder.

The invention also relates to the extract which may be obtained by the process of purification described above.

In addition, by virtue of its high titer of original anthrocyanosides and its low content of residual solvents, the extract may be used in any cosmetic, pharmaceutical or dietetic composition. It may also be used in nutraceutical compositions, functional foods, enriched foods and dietary supplements.

Figure 2:
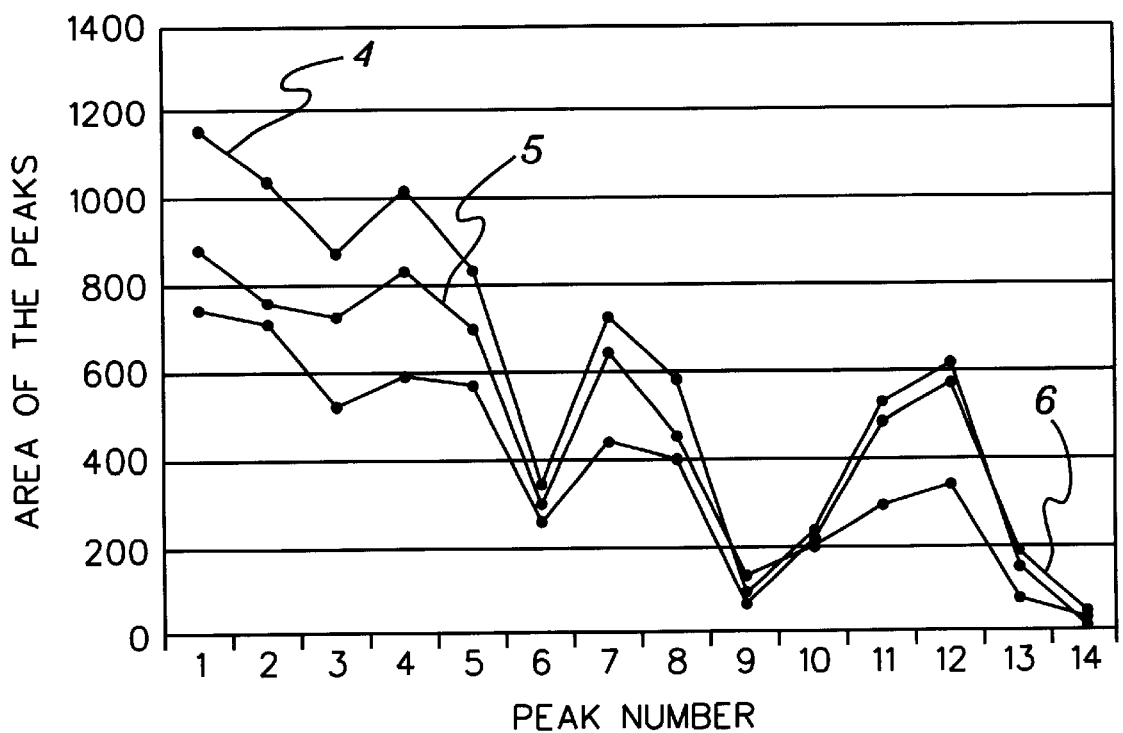
FIG. 2 is a graph of peak area vs. peak number which compares the HPLC chromatogram of the final extract of Example 2, in accordance with the process of the present invention, relative to that of the original fruit and that of the original pulp.

The invention and the advantageous which result therefrom will emerge more clearly from the following examples of implementation, in support of the appended figures in which:

FIG. 1 is a comparison of an HPLC chromatogram of the final extract obtained according to example 1 relative to that of the original fruit and that of the original pulp;

FIG. 2 is an identical comparison carried out starting with the extract obtained according to example 2.

The two examples which follow relate to the extraction of anthocyanosides from bilberry pulp.

EXAMPLE 1

1/Separation of the Pulp 125 kilos of bilberries from Lithuania are pressed by any known means. After pressing, the pulp representing 52.24 kilos and the juice representing 71.48 kilos are separated.

2/Extraction

Two successive extractions are then carried out starting with 35 kilos of bilberry pulp with each time 210 liters of methanol (that is 1 volume of pulp per 6 volumes of extraction solution) for twenty minutes at room temperature. At the end of the extraction, the pulp is pressed so as to recover the methanolic fraction. The methanol is then evaporated off under vacuum, the temperature of the extract then being equal to 22° C.

3/Purification

The concentrate is then taken up in 70 liters of demineralized water (that is one volume of pulp per 2 volumes of water).

The aqueous extract thus obtained is then stored at a temperature of less than 15° C. overnight.

The solution is then filtered on a 50 micrometer stainless steel gauze.

A macrocrosslinked resin, for example the resin XAD761 marketed by ROHM & HAAS, is then loaded with the aqueous extract. 25 liters of resin are used in practice.

Once the resin has been loaded, it is rinsed with 105 liters of demineralized water (that is one volume of pulp per 3 volumes of demineralized water).

The resin is then eluted with 200 liters of ethanol at 40%.

The eluate is then concentrated under vacuum, the temperature of the extract then being between 26 and 31° C.

To obtain a powder, the eluate is then spray-dried.

The anthocyanoside content of the final extract is equal to 50.46% of the final weight, that is 53.50% by weight of dry matter.

These results are expressed relative to cyanidin chloride, a standard used for HPLC analysis, reference 0909S, supplier: Extrasynthèse.

It is observed that the residual quantity of solvent in the final extract is:

0 ppm for butanol,
less than 3000 ppm for methanol,
less than 2000 ppm for ethanol.

The results of a chromatogram produced by HPLC of the final extract (1) relative to that of the original fruit (2) and pulp (3) are presented in FIG. 1.

As shown in this chromatogram, the profile for the extracted anthocyanosides is identical to that for the native anthocyanosides present in the original pulp or fruit, thus indicating that the physicochemical characteristics of the anthocyanosides are not adversely altered throughout the extraction and purification process.

It is therefore possible to think that the extract obtained, whose anthocyanoside composition is identical to that present in the original fruit, retains all the recognized qualities of the fruit.

EXAMPLE 2

Example 1 is reproduced starting with a second batch of bilberries from Poland.

It is observed that the anthocyanoside concentration obtained is equal to 49.1% by weight of the final extract, that is 52.01% by weight of dry matter.

The residual quantity of solvents is:

0 ppm for butanol,
less than 3000 ppm for methanol,
less than 2000 ppm for ethanol.

As above, FIG. 2 represents the HPLC chromatogram for the pulp for the fruit and for the extract obtained.

It is observed, in an identical manner, that the profile for the anthocyanosides contained in the extract (4) is identical to that contained in the pulp (5) and the fruit (6).

COMPARATIVE EXAMPLE 3

In this example, a comparison is made of various characteristics of commercial bilberry extract, respectively:

a bilberry extract marketed by the company INDENA called ANTHOCYANOSIDE;

and a second bilberry extract marketed by the company VINYALS called BILBERRY DRY EXTRACT (25% anthocyanosidine);

relative to an extract produced according to the process of the invention.

The criteria selected are:

the anthocyanoside concentration calculated by HPLC relative to a cyanidin chloride standard;

the residual quantity of solvent in the final extract.

The results are presented in the following table.

|  | INDENA SPECIFICATION | VINYALS SPECIFICATION | INVENTION SPECIFICATION | INVENTION RESULT |
|---|---|---|---|---|
| Anthocyanosides | 23.75–26.25% | 23.75–26.25% | 45–55% | 51.80% |
| Residual organic solvents | ≦30,000 ppm | ≦30,000 ppm | ≦3000 ppm | 1035 ppm |
| ethanol | ≦30,000 ppm | ? | ≦2000 ppm | 890 ppm |
| methanol | ≦300 ppm | ? | ≦300 ppm | 145 ppm |
| other solvents | ≦50 ppm | ? | ≦1 ppm | ≦1 ppm |
| Chromatographic profile | not determined | not determined | original fruit | superposition of the two profiles |

As shown in the table, the extract obtained according to the process of the invention makes it possible to obtain a very high anthocyanoside concentration compared with the commercial extract.

A very low residual quantity of organic solvent is also observed.

Finally, while nothing is indicated in the specifications for the INDENA and VINYALS extracts as regards the chromatographic profile, it is observed that the chromatographic profile for the extract of the invention may be superposed on that for the original fruit.

The advantages of the invention as regards the restitution in the extract of the native anthocyanosides of fruits are clearly evident from the description.

The use of conventional extraction solvents, which are removed throughout the process such that residual solvents are only present in trace amounts in the extract obtained, will be noted in particular.

Likewise, the process does not require the use of $SO_2$-type adjuvants to the extraction solvents or of chemical compounds, whose removal is highly delicate and poses a number of environmental problems.

Moreover, it is observed that the anthocyanosides are not denatured throughout the process and preserve a composition identical to that of the original fruit, thus making it possible to preserve their entire activity.

Finally, the anthocyanoside concentration of the extract obtained, which is in the region of 50% by weight of dry matter, should be emphasized.

What is claimed is:

1. A process for purifying a red fruit extract containing anthocyanosides comprising the steps of:
   (A) taking up said extract in an aqueous solution;
   (B) cooling said aqueous extract until a homogeneous temperature of less that 15° C. is reached;
   (C) filtering said cooled aqueous extract to obtain a permeate;
   (D) recovering said permeate;
   (E) loading said permeate onto a macrocrosslinked polymeric resin;
   (F) rinsing said loaded resin with demineralized water;
   (G) eluting said rinsed resin with an alcoholic eluting solution to obtain an eluate;
   (F) concentrating, then drying, said eluate.

2. The process according to claim 1, characterized in that the aqueous extract is cooled until it reaches a homogeneous temperature of less that 10° C.

3. The process according to claim 1, characterized in that the red fruit extract on which the purification is carried out is obtained according to the following steps:
   (A) separating a pulp from a whole red fruit;
   (B) bringing said pulp into contact with an extraction solution to produce a solid phase and a liquid phase;
   (C) separating said solid phase from said liquid phase; and
   (D) evaporating under vacuum at least some of the residual extraction solution contained in said liquid phase to obtain a concentrate.

4. The process according to claim 3, characterized in that said extraction solution contains a solvent selected from the group consisting of methanol, ethanol, butanol and acetone.

5. The process according to claim 1, characterized in that the purification is carried out on a prepurified extract provided in powdered form or in liquid form.

6. The process according to claim 1, characterized in that said alcoholic eluting solution is an aqueous solution of ethanol having an ethanol concentration between 10 and 90%.

7. The process according to claim 5, characterized in that said alcoholic eluting solution is an aqueous solution of ethanol having an ethanol concentration equal to 40%.

* * * * *